(12) United States Patent
Besson-Faure et al.

(10) Patent No.: US 6,168,925 B1
(45) Date of Patent: Jan. 2, 2001

(54) GPIIB/IIIA PLATELET RECEPTORS ASSAY

(75) Inventors: Isabelle Besson-Faure, Marseilles; Michel Canton, Cassis, both of (FR)

(73) Assignee: Biocytex, Marseilles (FR)

( * ) Notice: Under 35 U.S.C. 154(b), the term of this patent shall be extended for 0 days.

(21) Appl. No.: 09/147,654

(22) PCT Filed: Jun. 4, 1998

(86) PCT No.: PCT/FR98/01135

§ 371 Date: Feb. 8, 1999

§ 102(e) Date: Feb. 8, 1999

(87) PCT Pub. No.: WO98/55868

PCT Pub. Date: Dec. 10, 1998

(30) Foreign Application Priority Data

Jun. 6, 1997 (FR) .................................................. 97 07059

(51) Int. Cl.⁷ ........................ C07K 16/28; G01N 33/536
(52) U.S. Cl. ........................ 435/7.1; 435/7.21; 435/7.24; 530/388.22; 530/388.7; 530/388.25
(58) Field of Search ............................ 435/7.2, 7.1, 7.24; 530/388.22, 388.25, 388.7

(56) References Cited

U.S. PATENT DOCUMENTS

| | | | |
|---|---|---|---|
| 4,918,004 | * | 4/1990 | Schwartz . |
| 5,196,309 | * | 3/1993 | Ginsberg . |
| 5,387,413 | * | 2/1995 | Coller et al. . |
| 5,427,913 | * | 6/1995 | Shaw et al. . |
| 5,470,738 | * | 11/1995 | Frelinger, III et al. . |

FOREIGN PATENT DOCUMENTS

96/10749   4/1996   (WO) .

OTHER PUBLICATIONS

B.S. Coller et al., "Rapid and Simple Platelet Function Assay to Assess Glycoprotein IIb/IIIa Receptor Blockade", Circulation Vo. 95, No. 4, Feb. 18, 1997, pp. 860–867 (XP–002057028).

D. Cox et al., "Pentamidine is a Specific, Non–Peptide, GPIIb/IIIa Antagonist", Thrombosis and Haemostasis, vol. 3, No. 75, Mar. 1996, 7 pages (XP–002057029).

Weiss, E et al., Tisue Antigens, 46:374–381, 1995.*

Patel et al., Thrombosis and Haemostasis, 69, p. 706, Abstract, 1993.*

* cited by examiner

*Primary Examiner*—David Saunders
*Assistant Examiner*—Amy DeCloux
(74) *Attorney, Agent, or Firm*—Foley & Lardner

(57) ABSTRACT

The present invention relates to a method of determining, on a test sample, the occupation of the cellular GPIIb/IIIa receptor by an antagonist of fibrinogen, characterized in that the number of receptors occupied is determined in the said sample with the aid of an antibody MAb1 which is a competitor for the antagonist, and the total number of occupied or unoccupied receptors is determined with the aid of a so-called noncompetitor antibody MAb2 specific for the occupied or unoccupied receptor and the rate of occupation of the GPIIb/IIIa receptors in the sample is deduced therefrom.

14 Claims, 4 Drawing Sheets

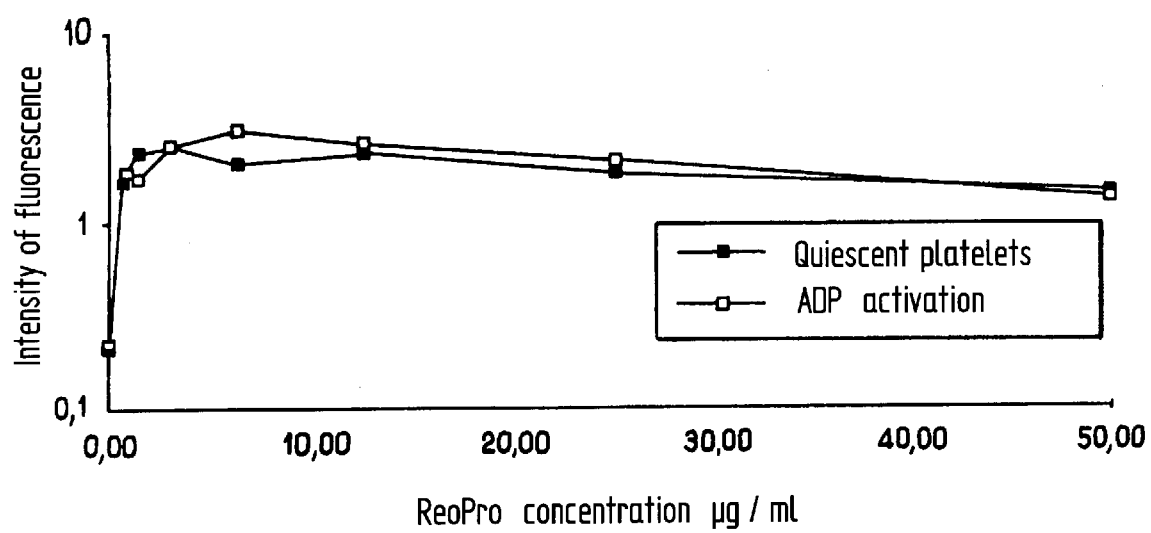
FIG_1
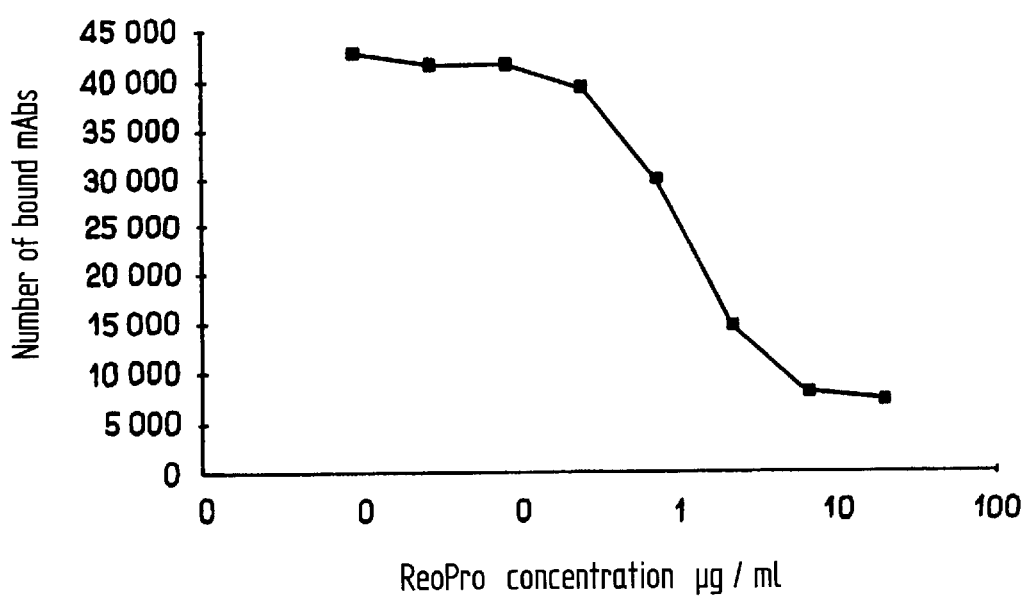
FIG_2

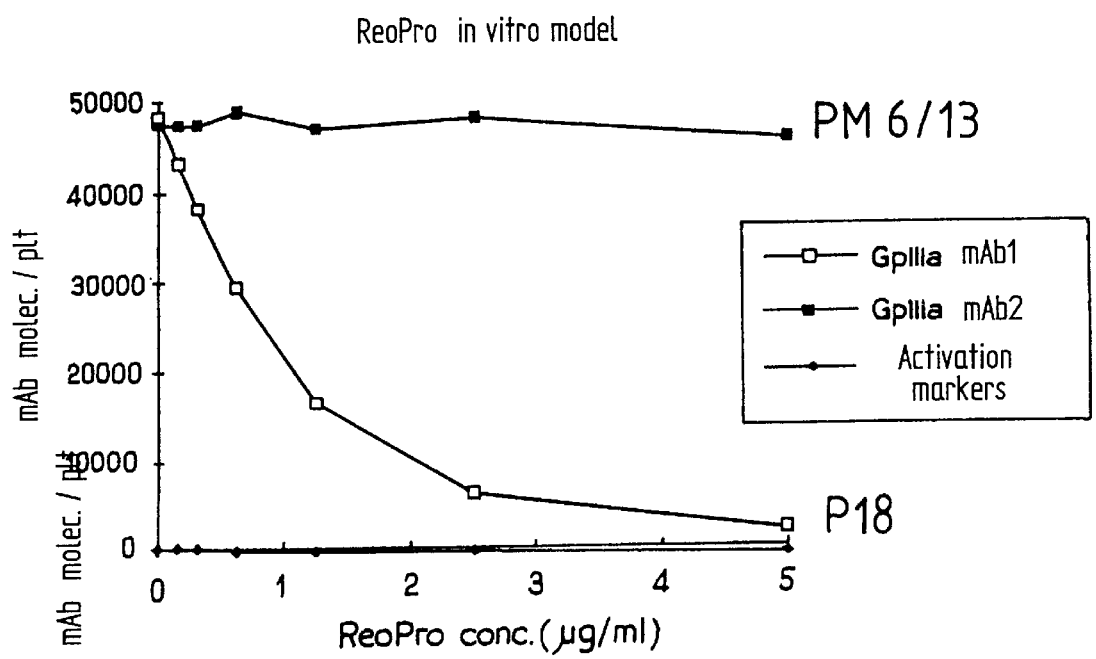
FIG._4
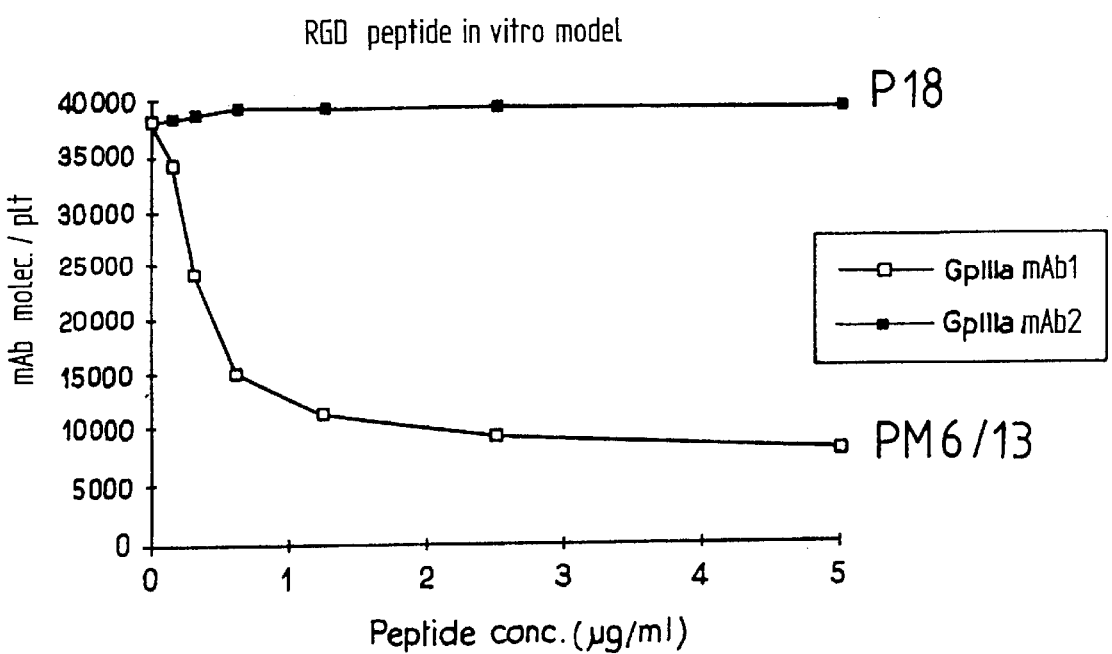
FIG._5

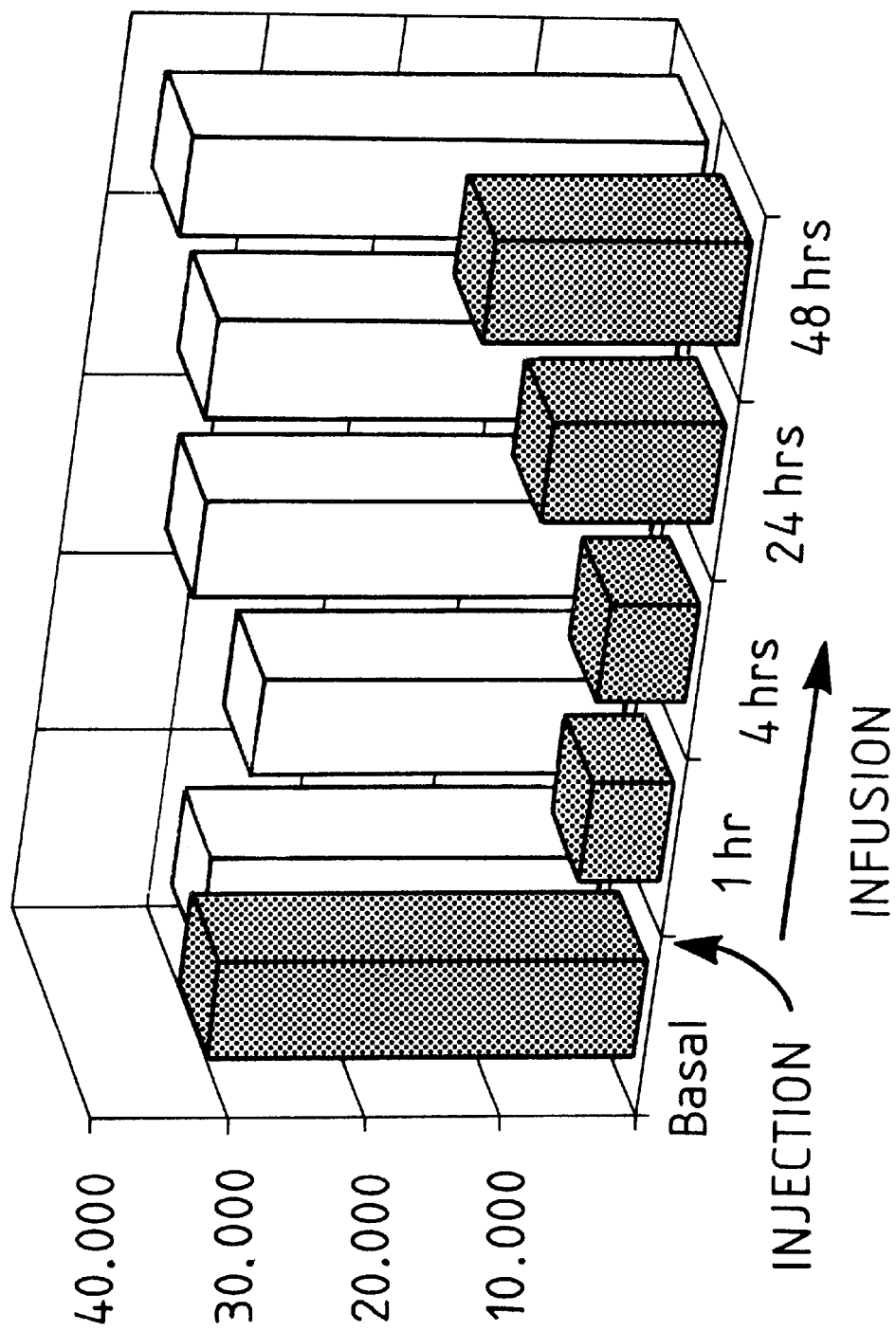
FIG_6

GPIIB/IIIA PLATELET RECEPTORS ASSAY

This application is a national stage filing under 35 USC 371 from PCT/FR98/01135, filed Jun. 4, 1998.

The invention relates to a method of analysing the platelet GPIIb/IIIa receptors occupied by an anti-platelet aggregation compound or by fibrinogen and the receptors which have remained in the free state.

The platelets play a key role in the equilibrium of the haemostatic balance. Activating signals can cause, at their level, both morphological and biochemical modifications together with variations in the levels of expression of surface glycoproteins. These glycoproteins are, for most ligand receptors, involved in adhesion (eg. the receptor for the von Willebrand factor: the molecule GPIb), in aggregation (eg. the receptor for fibrinogen: the molecule GPIIb/IIIa) whereas others indicate the state of platelet activation (eg. the molecule GMP 140 or P-selectin).

The activation of platelets and the aggregation resulting therefrom are physiological phenomena which, after exceeding a threshold, are associated with various pathological conditions such as arterial thrombotic accidents. This explains the reason for the interest which the pharmaceutical industry has for developing new anti-aggregation therapeutic molecules.

The preferred target in the new therapies developed is the GPIIb/IIIa receptor which is specifically expressed on the platelets. Under the effect of an activation of the platelets, this receptor binds, with a very high affinity, fibrinogen and other adhesion proteins, which causes aggregation of the platelets with each other.

The GPIIb/IIIa receptor belongs to the group comprising the integrins, which is composed of various molecules involved in the phenomena of cell adhesion. The integrins are a/p heterodimers and are classified into several families according to their β-subunit. About twenty integrins are currently known, of which 9 bind to their ligand via the amino acid sequence R—G—D.

GPIIb/IIIa ($\alpha$II$\beta$3) is a member of the family of $\beta$3 integrins. It has the same $\beta$ subunit (but a different $\alpha$ subunit) as the vitronectin receptor ($\alpha$v$\beta$3) present especially on the platelets and, in a large quantity, on the endothelial cells. The IIb and IIIa subunits are classified respectively into the CD 41 and CD 61 groups according to the international nomenclature.

The anti-platelet GPIIb–IIIa anti-aggregation agents belong to two different classes: a) the monoclonal antibodies which are antagonists of fibrinogen, including C7E3Fab of the humanized 7E3 monoclonal antibody directed against an epitope of CD 61 and marketed under the name a 7E3 monoclonal antibody solid under the tradename REOPRO®, b) the cyclic peptides, of the integrelin type, which possess the sequence RGD or KGD, close to the RGD sequence (Arg—Gly—Asp) common to the platelet receptor ligands, and the peptidomimetics, of the lamifiban or tirofiban type. These currently developed substances are only active by the parenteral route. Other molecules which can be administered by the oral route are being developed. These new molecules may, however, induce side effects which result in the patients treated in haemorrhagic effects at the points of access or of internal location. For these new molecules which, by their nature, remain in circulation for a long time, there is currently no antidote. It is therefore important, in the context of an anti-platelet therapy, to be able not only to adapt the therapeutic dose of the agent administered, but also to rapidly have available, during the monitoring of the treatment, information on the number of GPIIb/IIIa receptors occupied by the antagonist, so as to be able to control the haemorrhagic complications while preserving a sufficient quantity of bound antagonist in order to obtain an anti-aggregation effect.

Accordingly, the present invention relates to a method of determining, on a test sample, the occupation of the GPIIb/IIIa receptor, by an antagonist of fibrinogen, characterized in that the number of receptors occupied is determined with the aid of an antibody [MAb1] which is a competitor for the antagonist, and the total number of occupied or unoccupied receptors is determined with the aid of a so-called noncompetitor antibody [MAb2] specific for the occupied or unoccupied receptor and the occupation of the GPIIb/IIIa receptors in the sample is deduced therefrom.

BRIEF DESCRIPTION OF THE DRAWINGS

FIG. 1 shows the determination of the saturating concentration of a 7E3 monoclonal antibody sold under the tradename ReoPro® on a platelet at the basal state and after activation with ADP.

FIG. 2 shows that when the a 7E3 monoclonal antibody sold under the tradename ReoPro® preincubation concentration is varied in a dose/response experiment with protocol 3, the binding of P18 is inversely proportional to that of the anti-aggregation agent.

FIG. 4 shows an in vitro model on whole blood with a 7E3 monoclonal antibody sold under the tradename ReoPro® as an anti-aggregation agent using PM6/13 as Mab2 and P18 as Mab1.

FIG. 5 shows an in vitro model on whole blood with RGD peptide as an anti-aggregation agent using PM6/13 as Mab2 and P18 as Mab1.

FIG. 6 shows the number of free receptors after the injection relative to the total number of receptors—has been inserted on page 3, between lines 9 and 10.

Figure 3:
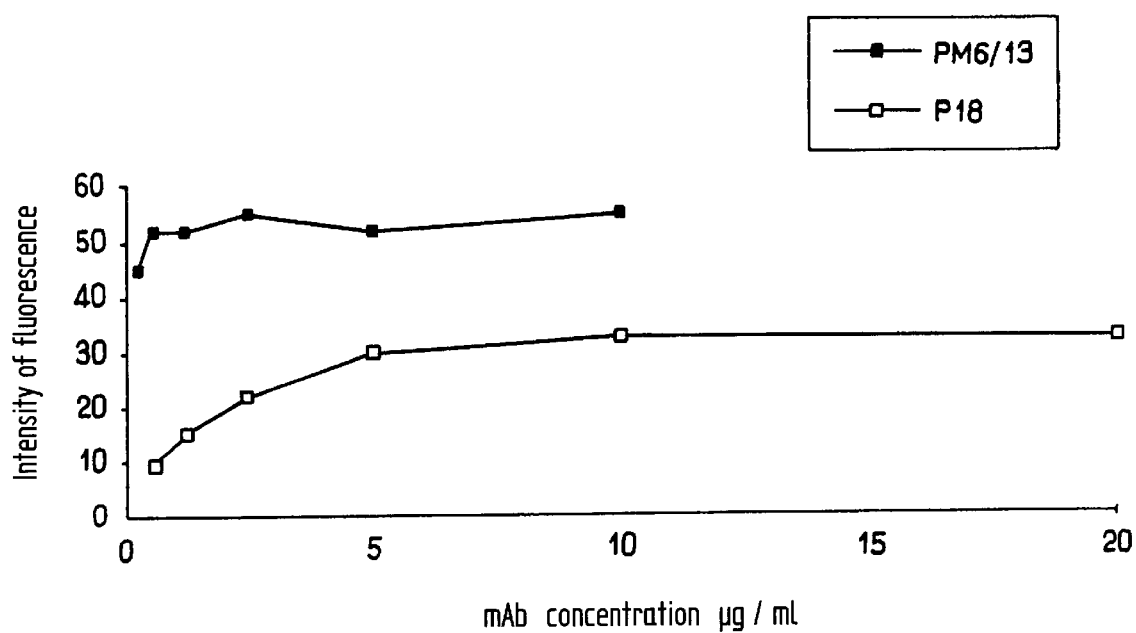
FIG. 3 is a saturation study on platelets for purified mabs CD 61 P18 and PM 6/13.

Occupation is understood to mean both the quantification, in absolute numerical terms, of the platelet receptors for fibrinogen GPIIb/IIIa occupied by an anti-aggregation agent compared with the total number of receptors in a blood sample, and a ratio whose variation may be studied over time.

It is also possible to determine the total number of receptors before any medication without having to repeat this determination in the context of the monitoring of the treatment.

Likewise, when it is specified that the number of receptors is determined, this may only be a semiquantitative determination.

Of course, when it is desired to precisely measure the number of receptors, it is necessary to provide calibration series with calibration curves.

The anti-GPIIb/IIIa antibodies used in the context of the present invention are preferably directed against an epitope of the GPIIIa(CD61) subunit.

They are more particularly the antibodies SZ 21 and P2 which are marketed by the company Immunotech and the antibody PM 6/13 which is marketed by the company Cymbus.

They may also be the monoclonal antibodies P18 deposited in the Belgian Coordinated Collection of Microorganisms (BCCM) under the number LMBP 1662CB on Jun. 5, 1997 (this deposit is only accessible to experts, in accordance with legal provisions).

The antibody, PM 6/13 is available from Cymbus Bioservices Limited (UK), it is an anti-CD 61 of the IgG1 SZ 21 type available from Immunotech (France) and an anti-CD 61 of the IgG1 type; as for P2 which is available from the same company, it is an anti-CD 41 IgG1.

The antibody pairs used will depend mainly on the type of anti-aggregation agent used. Indeed, a 7E3 monoclonal antibody sold under the tradename REOPRO® and peptides of the RGD type are anti-aggregation agents which bind to different sites of GPIIIa.

A 7E3 monoclonal antibody sold under the tradename REOPRO® has a site close to that for fibrinogen and inhibits its binding by steric hindrance; on the contrary, the RGD peptides have the same site as fibrinogen, in direct competition for the RGD sequence.

Because of this, the most suitable product for the determination of the receptors occupied by a 7E3 monoclonal antibody sold under the tradename REOPRO® is the pair consisting of the competitor antibody P2 from Immunotech and the noncompetitor antibody PM 6/13 from Cymbus, whereas in the case of the RGD peptides, the competitor antibody is the antibody PM 6/13 from Cymbus and the noncompetitor antibody is the antibody SZ 21 from Immunotech. Indeed, the antibody PM 6/13 is a noncompetitor antibody when the anti-aggregation agent is a 7E3 monoclonal antibody sold under the tradename REOPRO®, but becomes a competitor antibody if it is an RGD peptide.

The determination using the preceding mono-clonal antibodies is preferably a determination by quantitative cytometry, but other methods inspired in particular by Elisa or another type of method may be considered.

Preferably, the determination is carried out by revealing specific antibodies with the aid of antibodies labelled with a fluorochrome using, in particular, the indirect immunofluorescence method which may be combined with a quantitative method.

The so-called cytometric method, as well as the indirect quantitative immunofluorescence method (so-called IQIF method) are known and will not be described again in detail (P. Poncelet et al., 1985, J. Immunol. Methods 85, 65–74).

The sample used is preferably a biological sample, especially a blood sample, a sample of whole blood collected over sodium citrate or citrate theophilline adenosine dipyrridanol (CTAD) (inhibitor of the platelet functions), or alternatively a fraction rich in platelets, a plasma rich in platelets (PRP) or bound platelets for example.

Although specific antibody pairs have been previously mentioned it is possible to use other anti-bodies which may be selected in particular from the lists provided in the book entitled "Leucocyte Typing V, White Cell Differentiation Antigens; Proceedings of the Fifth International Workshop and Conference held in Boston, USA, Nov. 3–7, 1993, volume 2, Oxford University Press, 1995", since for the anti-GPIIb/IIIa competitor antibodies, there is selected an antibody directed against an epitope of the GPIIb/IIIa complex whose rate of binding thereto drops by at least 50% and preferably 75% in the presence of an anti-platelet aggregation agent used at saturating concentration, but whose binding should not inhibit that of the anti-aggregation agent to the platelets.

As regards the noncompetitor anti-GPIIb/IIIa antibody, it will be an antibody directed against an epitope of the GPIIb/IIIa pair whose rate of binding thereto does not vary more than 15% in the presence and in the absence of an anti-platelet aggregation agent.

The present invention also relates to an assay kit intended for carrying out the preceding method, characterized in that it comprises at least:

one monoclonal antibody for the GPIIb/IIIa receptor which is a competitor for a fibrinogen antagonist, and one monoclonal antibody specific for the occupied or unoccupied GPIIb/IIIa receptor.

The principle of the quantification of surface antigens such as the GPIIb/IIIa receptors can be briefly recalled here.

The cellular antigenic sites to be quantified are labelled in indirect immunofluorescence, with binding of an mAb, preferably of the IgG type and in particular from mice, specific for the antigen to be studied, revealed by an antimouse IgG polyclonal conjugated with a fluorochrome. The intensity of fluorescence obtained in flow cytometry is an arbitrary unit which is, however, closely linked to the cellular level of expression of the antigen. Standardization of the cytometric data is provided by the introduction, during each immunolabelling, of a calibrating substance treated in parallel with the sample tubes. This calibrating substance consists of latex beads coated with increasing and defined quantities of IgG-type mAb. Analysis of this calibrating substance allows the preparation of a calibration series linking the intensities of fluorescence to the absolute number of antigens per cell.

The examples below make it possible to demonstrate the characteristics and advantages of the present invention.

The test provided is carried out on a sample of whole blood collected over sodium citrate (or CTAD). In the CYTOQUANT Gp model, the labelling technique is performed directly on whole blood and does not require a washing step. For this test, three parameters are studied per sample (3 tubes): the blood is placed in contact with a negative-control mAb (nonspecific labelling), an mAb Mab1 and an mAB MAb2. The calibration series is added to one tube during the second labelling step, in the presence of the fluorescent revealing Ab. The intensity of fluorescence due to the immunolabelling is then read on a cytometer. This intensity of fluorescence is proportional to the number of specific mAb bound to the platelets. Conversion of the intensity of fluorescence into absolute number of mAB bound per platelet is carried out after construction of the calibration straight line.

The results are expressed in the following manner:

total number of molecules of GPIIb/IIIa per platelet (MAb2 value)

number of GPIIb/IIIa molecules occupied by the anti-aggregation molecule (MAb2-MAb1 difference).

Thus, two parameters may be studied at the same time.

EXAMPLE 1

During the feasibility phase, various mAbs specific for GPIIb/IIIa were tested on platelets in the presence and in the absence of a 7E3 monoclonal antibody sold under the tradename REOPRO®.

Determination of the saturating concentration of ReoPro on a platelet at the basal state and after activation with ADP

Protocol 1

The indirect immunofluorescence test by replacing the specific mAb with a 7E3 monoclonal antibody sold under the tradename REOPRO® at different dilutions.

1—Materials a 7E3 monoclonal antibody sold under the tradename REOPRO® 2 mg/ml, dilutions in 0.1% PBS-BSA from 50 µg/ml→0.75 µg/ml ADP Stago 0.2 µM

DDAF

2—Method

| Mix vol/vol | PRP/dilutions of a 7E3 monoclonal antibody sold under the tradename REOPRO ® (mix 1) PRP/PBS buffer (mix 2) |
|---|---|
| Incubation 15 min RT | |
| Mix vol/vol | mixture 1/PBS mixture 1/ADP 0.2 μM mixture 2/PBS mixture 2/ADP 0.2 μM |

Incubation 5 min RT
To each of the mixtures, add 4 ml PBS BA. Centrifugation 3000 rpm 10 min.

Remove the supernatant.
Pellet+100 μl DDAF (sheep anti-mouse-FITC reagent)
Incubation 15 min RT
+2 ml PBS→FCM analysis N. B. There are as many mixture 1 tubes as ReoPro dilutions.

a 7E3 monoclonal antibody sold under the tradename REOPRO® is a chimeric F(ab)-type Ab with an immunoreactive mouse Fv portion combined with a constant human IgG portion. The second reagent, an FITC-conjugated anti-mouse Ig sheep polyclonal, binds weakly to the ReoPro molecule but sufficiently to obtain an analysable signal. The saturating concentration is from 1 μg/ml final concentration. Platelet activation with ADP does not modify the binding of a 7E3 monoclonal antibody sold under the tradename REOPRO®.

The results of the test are presented in FIG. 1.
Identification of mabs which are, on the one hand, complementary and, on the other hand, competitors for the binding of ReoPro Protocol 2

1—Materials
a 7E3 monoclonal antibody sold under the tradename REOPRO® 2 mg/ml diluted to 10 μg/ml in 0.1% PBS BSA
MAbs CD41 and CD61 (anti-GPIIb/IIIa and anti-GPIIIa) at 10 μg/ml.
DDAF (sheep anti-mouse Ig-FITC).

2—Method

| Mix vol/vol | PRP/a 7E3 monoclonal antibody sold under the tradename REOPRO ® 10 μg/ml PRP/PBS BSA 0.1% |
|---|---|

Incubation 5 min RT

Washing of the 2 mixtures (+4 ml PBS BSA 0.1%, centrifugation 3000 rpm 10 min, remove the supernatant).

Pellet+PBS BSA (vol=initial vol of PRP)

20 μl of each mixture+20 μl of each MAb to be tested.

Incubation 10 min RT

+100 μl DDAF 1/100

Incubation 10 min RT

+2 ml PBS BSA 0.1% →FCM analysis

We tested 9 mAbs specific for GPIIb/IIIa (CD41 and CD61) (see Table 1).

TABLE 1

| | RGD PEPTIDE | | B14 | |
|---|---|---|---|---|
| | TYPE | % INHIBITION | TYPE | % INHIBITION |
| P18 (BIOCYTEX) | Stable | 3 | Competitor | 98 |
| PM6/13 (CYMBUS) | Competitor | 83 | Stable | 7 |
| SZ21 (IMMUNOTECH) | Stable | 0 | Stable +/− | 14 |
| P2 (IMMUNOTECH) | Competitor | 76 | Competitor | 99 |
| M148 (CYMBUS) | Stable +/− | 12 | Stable | 1 |
| 1PLA SD5 (BIOCYTEX) | Stable | 0 | Competitor | 100 |
| 1PLA 4F8 (BIOCYTEX) | Competitor | 79 | Stable | 0 |
| P1 (INSERM) | Stable +/− | 26 | Stable +/− | 11 |
| P6 (INSERM) | Stable | 6 | Stable | 0 |

Test carried out on whole blood in the absence of a drug (100%), and in the presence of a saturating concentration of anti-aggregation agent inhibiting the binding of fibrinogen.

We compared the quantitative values obtained on platelets preincubated in the presence of ReoPro (10 μg/ml final) or of PBS. We chose the mAb PM6/13 whose expression does not vary by more than 10% in the presence and in the absence of a 7E3 monoclonal antibody sold under the tradename REOPRO® and the mAb P18 whose expression drops by more than 95% in the presence of a 7E3 monoclonal antibody sold under the tradename REOPRO® used at saturating concentration.

Table 1 shows the results obtained with the same antibodies tested on whole blood.

The advantage of using the PM16/13-P18 pair lies in the comparable response observed on a platelet for the 2 mAbs, in the absence of anti-aggregation agent.

When the a 7E3 monoclonal antibody sold under the tradename REOPRO® preincubation concentration is varied, in a dose/response experiment with protocol 3, the binding of P18 is inversely proportional to that of the anti-aggregation agent as indicated in FIG. 2.

Conclusion
Specificity: Mab1 clone P18 (CD61, anti-GPIIIa) Mab2 clone PM6/13 (CD61, anti-GPIIIa)
Source: Clone P18 (mAb IgG2a INSERM Clone PM6/13 (Mab IgG1) Cymbus
A sheep (Fab)'$_2$ anti-mouse total Ig—FITC reagent, DDAF, constitutes the most appropriate polyclonal reagent.
FIG. 3 is a saturation study on platelets for purified mAbs CD 61 P18 and PM 6/13.

Protocol 3

1—Materials
a 7E3 monoclonal antibody sold under the tradename REOPRO® 2 mg/ml dilutions in PBS BSA 0.1%, 3-fold from 200 μg/ml to 0.09 μg/ml mAb P18: Ascite 1/800
mAb PM6/13: 10 μg/ml
DDAF
PRP 2—Method 1/10 dilution of each preparation of a 7E3 monoclonal antibody sold under the tradename REOPRO® in PRP. Incubation 5 min RT Washing (in PBS BSA 0.1% 3000 rpm 10 min)

Pellet+PBS BSA 0.1% (vol equal to the initial volume of PRP)

20 μl of platelet preparation+20 μl of mAb P18, PM6/13 and IgG, negative control.

Incubation 10 min RT

+100 μl DDAF 1/100 on each immunolabelling and on 40 μl of calibration series of the CYTOQUANT GP type. Incubation 10 min RT +2 ml PBS BSA 0.1%→FCM.

EXAMPLE 2

Equivalent determinations were carried out using:
PM6/13 as Mab2, and
P18 as Mab1
in an in vitro model on whole blood with, as anti-aggregation agent, a 7E3 monoclonal antibody sold under the tradename REOPRO® at various concentrations.

The results are assembled in FIG. 4.

EXAMPLE 3

Equivalent assays were carried out using:
P18 as Mab2
PM6/13 as Mab1
in an in vitro model using, as anti-aggregation agent, the RGD peptide at various concentrations.

The results are assembled in FIG. 5.

In Examples 2 and 3, the drug used (a 7E3 monoclonal antibody sold under the tradename REOPRO® or RGD peptide) is diluted in a phosphate buffer in order to obtain a series of dilutions from 1 to 50 μg/ml. 5 μl are mixed with 45 μl of whole blood (1/10 dilution). The incubation is carried out at room temperature for 30' and then 150 μl of buffer are added.

To aliquots of 20 μl of diluted whole blood are added 20 μl of mAb tested at 10 or 20 μg/ml.

After incubation and addition of FITC-conjugated anti-mouse Ig Ab, a cytometric analysis is carried out.

The number of mAbs molecules bound by platelets is calculated using a calibration straight line plotted using latex beads, in accordance with the IQIF method.

EXAMPLE 4

Tests were carried out in vivo on patients treated with ReoPro.

In this case, a 7E3 monoclonal antibody sold under the tradename REOPRO® is not added. Whole blood is collected (20 μl diluted 1/4 in physiological buffer).

20 μl of mAb (P18 or PM 6/13) at 10 μg/ml are added. The incubation is carried out for 10' at room temperature (RT). 20 μl of reagent are then added and a cytometric reading is carried out after incubation (10' RT) and appropriate dilution.

FIG. 6 shows the number of free receptors after the injection relative to the total number of receptors. After 48 hours, the number of free receptors is still less than 50%.

The mAbs used are PM6/13 for the determination of the total receptors and P18 for the determination of the free receptors.

Claims:

1. A method for determining the occupation of cellular GPIIb/IIIa receptors by a platelet anti-aggregating agent, comprising the steps of (a) determining the number of occupied receptors with a first monoclonal antibody ("MAb1") which is a competitor for said agent by determining the number of MAb1 bound to the receptors;

(b) determining the number of total receptors with a second monoclonal antibody ("MAb2") which is a non-competitor for said agent by determining the number of MAb2 bound to the receptors; and (c) deducing the rate of occupation of the receptors by dividing the number of MAb1 bound with the number of MAb2 bound.

2. Method according to claim 1, characterized in that the number of receptors is measured by comparison with calibration curves.

3. Method according to claim 1, characterized in that the antibodies are directed against GPIIIa.

4. Method according to claim 1, characterized in that the determination is carried out by labeling the antibodies with the aid of a labeled antibody.

5. Method according to claim 4, characterized in that the antibody is labeled with a fluorochrome.

6. Method according to claim 5, characterized in that the determination is carried out by quantitative cytometry.

7. Method according to claim 6, characterized in that the determination is carried out by the indirect quantitative immunofluorescence method.

8. Method according to claim 1, wherein the Mab1 is the monoclonal antibody PM6/13, the Mab2 is the monoclonal antibody SZ21 and the agent is an RGD peptide.

9. Method according to claim 1, wherein the Mab1 is the monoclonal antibody P2, the Mab2 is the monoclonal antibody PM6/13 and the agent is the antibody 7E3 or fragments thereof.

10. Method according to claim 1, characterized in that the sample to be tested is a blood sample.

11. Method according to claim 10, characterized in that the sample to be tested is a sample enriched in platelets.

12. The method as set forth in claim 1, wherein said agent is a fibrinogen antagonist.

13. Assay kit intended for carrying out the method according to claim 1, characterized in, that it comprises at least:

one monoclonal antibody for the GPIIb/IIIa receptor which is a competitor for a platelet anti-aggregating agent, and one monoclonal antibody specific for the occupied or unoccupied GPIIb/IIIa receptor.

14. The kit of claim 13, wherein the agent is a Fibrinogen antagonist.

* * * * *